(12) United States Patent
Pratt et al.

(10) Patent No.: US 11,058,453 B2
(45) Date of Patent: Jul. 13, 2021

(54) SENSOR SYSTEMS FOR SKIN GRAFT HARVESTING

(71) Applicant: KCI Licensing, Inc., San Antonio, TX (US)

(72) Inventors: Benjamin A. Pratt, Poole (GB); Christopher Brian Locke, Bournemouth (GB); Timothy Mark Robinson, Blandford Forum (GB); Kevin Higley, San Antonio, TX (US); Tab Randolph, San Antonio, TX (US); T. Blane Sanders, San Antonio, TX (US)

(73) Assignee: KCI LICENSING, INC., San Antonio, TX (US)

(*) Notice: Subject to any disclaimer, the term of this patent is extended or adjusted under 35 U.S.C. 154(b) by 443 days.

(21) Appl. No.: 16/000,889

(22) Filed: Jun. 6, 2018

(65) Prior Publication Data

US 2019/0038303 A1 Feb. 7, 2019

Related U.S. Application Data

(62) Division of application No. 14/581,560, filed on Dec. 23, 2014, now Pat. No. 9,993,261.

(60) Provisional application No. 61/922,432, filed on Dec. 31, 2013.

(51) Int. Cl.
*A61B 17/322* (2006.01)
*A61B 17/00* (2006.01)
*A61B 17/30* (2006.01)

(52) U.S. Cl.
CPC .. *A61B 17/322* (2013.01); *A61B 2017/00026* (2013.01); *A61B 2017/00039* (2013.01); *A61B 2017/00061* (2013.01); *A61B 2017/00106* (2013.01); *A61B 2017/00119* (2013.01); *A61B 2017/00221* (2013.01); *A61B 2017/00951* (2013.01); *A61B 2017/308* (2013.01); *A61B 2017/3225* (2013.01)

(58) Field of Classification Search
CPC .......... A61B 17/322; A61B 2017/3225; A61B 2017/306; A61B 2017/308
See application file for complete search history.

(56) References Cited

U.S. PATENT DOCUMENTS

| | | | | |
|---|---|---|---|---|
| 2002/0169394 A1* | 11/2002 | Eppstein | .......... | A61B 5/150083 600/573 |
| 2012/0035619 A1* | 2/2012 | Sabir | ....................... | A61P 17/02 606/132 |
| 2012/0172894 A1* | 7/2012 | Sabir | ..................... | A61B 17/322 606/132 |
| 2013/0145596 A1* | 6/2013 | Sabir | ..................... | A61B 90/03 29/428 |
| 2013/0204273 A1* | 8/2013 | Sabir | ..................... | A61B 18/08 606/132 |

\* cited by examiner

*Primary Examiner* — Diane Dornbusch
(74) *Attorney, Agent, or Firm* — Foley & Lardner LLP

(57) ABSTRACT

Skin graft harvesting systems and methods are disclosed that utilize sensors to automate the harvesting of skin grafts or assist a user in deciding when the skin graft is ready to be harvested. Such systems and methods can reduce the burden of visual observation and ensure greater reliability and consistency of the grafts. The invention is particularly useful with harvesters that rely upon suction and/or heating to raise a plurality of small or "micro" blisters simultaneously.

23 Claims, 5 Drawing Sheets

SENSOR SYSTEMS FOR SKIN GRAFT HARVESTING

CROSS-REFERENCE TO RELATED APPLICATIONS

This application claims priority to and is a divisional of U.S. application Ser. No. 14/581,560, filed on Dec. 23, 2014, which granted as U.S. Pat. No. 9,993,261, and claims the benefit of and priority to U.S. Provisional Application No. 61/922,432, filed on Dec. 31, 2013. The entire teachings of these earlier applications are incorporated herein by reference.

FIELD OF THE INVENTION

The present invention generally relates to devices and methods for generating and harvesting skin grafts.

BACKGROUND

Skin is the largest organ of the human body, representing approximately 16% of a person's total body weight. Because it interfaces with the environment, skin has an important function in body defense, acting as an anatomical barrier from pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation (e.g., vitiligo).

Skin grafts are often used to repair such skin damage. Skin grafting is a surgical procedure in which a section of skin is removed from one area of a person's body (autograft), removed from another human source (allograft), or removed from another animal (xenograft), and transplanted to a recipient site of a patient, such as a wound site. Typically it is preferable to use an autograft instead of an allograft or a xenograft to reduce complications, such as graft failure and rejection of the skin graft.

A problem encountered when using an autograft is that skin is taken from another area of a person's body to produce the graft, resulting in trauma and wound generation at the donor site. Generally, the size of the graft matches the size of the recipient site, and thus a large recipient site requires removal of a large section of skin from a donor site, leading to increased pain and discomfort and longer healing time. Additionally, as the size of the section of skin removed from the donor site increases, so does the possibility of infection.

Techniques have been developed for harvesting a large number of smaller grafts, e.g., so-called micrografts, to reduce the trauma at the donor site. By removing only a fraction of the skin at a donor site and leaving regions of healthy skin surrounding the excised regions, a large amount of skin for transplantation can be obtained with less discomfort. Micrograft harvesting can also reduce the healing time and risk of infection at the donor site.

SUMMARY

Skin graft harvesting systems and methods are disclosed that utilize sensors to assist a user in deciding when the skin graft is ready to be harvested. Such systems and methods can reduce the burden of visual observation and ensure greater reliability and consistency of the grafts. The invention is particularly useful with harvesters that rely upon suction and/or heating to raise a plurality of small or "micro" blisters simultaneously.

In one embodiment, the sensor systems can include a matrix of proximity (non-contact) optical sensors, e.g., one or more light-emitters (e.g., laser, light-emitting diode or fiber light sources) and one or more detectors (e.g., photodetectors, photocells or photodiodes) arranged such that the path of light from the light-emitter to the detector is at least partially interrupted when a skin blister reaches a point suitable for harvesting.

The emitter can produce a signal that will be received by the detector. In certain embodiments, a single emitter can be paired with multiple sensors by directing the signal in multiple directions. Utilizing single emitters paired with multiple sensors can reduce complexity and cost by reducing the number of components in the system. The signal can be a continuous beam or a series of timed pulses to keep power consumption to a minimum (and reduce the heating effects due to irradiation of the harvested skin).

When a sensor does not receive an expected signal it can be assumed that the direct line of travel between the emitter and sensor has been broken and that therefore the blister has achieved a sufficient height ready for harvesting.

Due to the dynamic nature of blister formation, it may be advantageous to take repeated sensor readings before an alert is given that the site is ready for harvesting. In microblister systems it may also be desirable to set a threshold, e.g., when a pre-assigned number of sensors are in a 'ready' state, before giving an alert to the user that the site is ready for harvesting.

When the conditions have been met or a determination is otherwise made by the system that the skin is ready for harvesting, the device can instruct the user to do so. Alternatively, the system can be automatic, e.g., actuating the harvester to cleave the blisters as soon as certain conditions are met.

In one aspect of the invention, methods for preparing a skin graft can include the steps of applying a blister cutting device to a donor site on a subject's skin; applying a negative pressure within the device to thereby raise at least one blister at the donor site; and monitoring the formation of the blister with a sensor. The method can further include transmitting information from the sensor to alert the user when the blister has reached a state suitable for harvesting, e.g., by transmitting information from the sensor to a controller. Upon receipt of the information from the sensor to a controller reduce or terminate the negative pressure, alert the user and/or activate the cutter device to cleave the blister.

In one embodiment, monitoring the formation of the blister within the device can further include deploying a sensor comprising at least one emitter-receiver pair within the device and emitting a signal from the emitter and receiving the signal with the receiver. The emitter can emit electromagnetic radiation or acoustic waves and the receiver is capable of detecting such radiation or acoustic wave. A disruption in the signal reception can thus indicate the presence of a skin blister.

In another embodiment, the sensor is disposable in close proximity to a growing blister and configured to sense the presence of a blister by detecting changes in electrical, magnetic or optical behavior of a sensor element. For example, the sensor can be a load sensor disposable in close proximity to a growing blister and configured to sense the presence of a blister by a pressure the blister asserts on the load sensor. Alternatively, or in addition, the sensor can be a conductivity sensor disposable in close proximity to a growing blister and configured to sense the presence of a blister by a pressure the blister asserts on the conductivity sensor.

In another embodiment, the sensor can be a color sensor and step of monitoring the formation of blisters within the device further comprises detecting changes in color within the device. For example, the sensor can be a colorimetric sensor capable of detecting changes in color in a plate having the holes through which the blisters will be raised.

In yet another embodiment, the sensor can be an acoustic sensor and the step of monitoring the formation of blisters within the device further comprises detecting changes in the acoustics of the device. For example, the sensor can be an ultrasound sensor and the step of monitoring the formation of blisters within the device further comprises detecting changes in an acoustic signature or image obtained within the device.

In a further embodiment, the sensor can be a vacuum sensor and the step of monitoring the formation of blisters within the device further comprises detecting changes in a negative pressure within the device or by deducing volume changes within the device by measuring the time required to reach a negative pressure level within the device.

In another aspect of the invention, the method can employ a cutting device that includes at least one fixed plate and at least one movable cutter plate, each plate having a plurality of holes through which suction blisters can be raised when the holes of the fixed and movable plates are aligned, and the step of cleaving the blisters further comprises moving the cutter plate to disrupt alignment of the holes and thereby separate the blisters from remaining skin at the donor site. The method can further include delivering a warm hypotonic fluid to a chamber within the device such that skin exposed to the chamber via the plate holes can assimilate fluid before and/or after applying negative pressure to the chamber to pull skin into the chamber through the holes and thereby raise a plurality of blisters.

More specifically, the methods for preparing a skin graft according to the invention can be practiced with a device comprising a device body, a sealing head member, at least one fixed plate and at least one movable cutter plate, each plate comprising a plurality of holes and wherein as assembled the holes in the plates are aligned within the body, the method including the steps of: connecting the device to a donor site on a subject's skin; joining the sealing head member and body together to define a sealed chamber; applying negative pressure to the chamber to pull skin into the chamber through the holes and thereby raise a plurality of blisters; monitoring the formation of blisters with one or more sensors; detecting when the blisters are in a condition suitable for harvesting (e.g., based on a signal or loss of signal from a sensor); unsealing the chamber; applying an adhesive substrate to the exposed blisters within the chamber; actuating the movable cutter plate to disrupt the alignment of the holes and to cut the blisters; and removing the substrate together with the cleaved skin blisters.

In another aspect of the invention, devices are disclosed for obtaining a skin graft, the devices including a body that is disposable on a patient's skin; a head adapted for coupling to a cutting body, the head further comprising a sealing surface to engage with a mating surface on the cutting body such that, when the head is engaged with the body on a patient's skin, a sealed chamber is formed over a target region of skin; and a negative pressure conduit also connected to the chamber and adapted for applying negative pressure within the chamber to raise at least one skin blister within the chamber; a sensor for monitoring the formation of the blister; and a cutter mechanism within the body for cleaving the blister after formation.

In some embodiments, the sensor is configured to alert the user when the blister has reached a state suitable for harvesting. Alternatively, the device can also include a controller for receiving information from the sensor. The controller can be configured to reduce or terminate the negative pressure or to activate the cutter mechanism and cleave the blister based on information from the sensor.

In certain embodiments, the sensor can include at least one emitter-receiver pair within the device such that the emitter is configured to emit a signal and the receiver is configured to receive the signal, and wherein a disruption in the signal reception or a change in signal strength indicates the presence of a skin blister. Alternatively, the sensor is situated within the device such that it can be deployed in close proximity to a growing blister, and configured to sense the presence, e.g., the size and/or height of the blister by detecting changes in electrical, magnetic or optical behavior of a sensor element. In another alternative embodiment, the sensor can be a load sensor disposable in close proximity to a growing blister and configured to sense the presence of a blister by a pressure the blister asserts on the load sensor. For example, the sensor can be a conductivity sensor disposable in close proximity to a growing blister and configured to sense the presence of a blister by a pressure the blister asserts on the conductivity sensor.

In other embodiments, the sensor can be a color sensor configured to detect the formation of blisters within the device based on detected changes in color within the device. For example, the sensor can be a colorimetric sensor capable of detecting changes in color in the plate having the holes through which the blisters will be raised.

In another embodiment, the sensor can be an acoustic or ultrasound sensor capable of monitoring the formation of blisters within the device by detecting changes in the acoustics and/or an acoustic signature or image obtained within the device.

In yet another embodiment, the sensor can be a vacuum sensor capable of monitoring the formation of blisters within the device by detecting changes in a negative pressure within the device or by deducing volume changes within the device, e.g., by measuring the time required to reach a negative pressure level within the device.

In certain embodiments of the invention, a two part device for harvesting of skin microblisters is disclosed. The two parts are a harvester body that is adapted for attachment to a target region of skin and a harvester head, which delivers heat and/or negative pressure to at least portions of the skin engaged by the harvester body.

More specifically, the head is adapted for coupling to a cutting body ("harvester") that is disposable on a patient's skin and further adapted for coupling to a vacuum source, the head further providing a sealing surface to engage with a mating surface on the cutting body such that, when the head is engaged with the cutting body on a patient's skin, an evacuated chamber is formed over a target region of skin; and, preferably, the sensor system is disposed within the chamber to monitor that blisters as they are formed.

Optionally, in addition to defining at least a portion of a negative pressure chamber, the head can further include a heating element that is a resistive electrical heating element or a mechanism for infusing a heated fluid. In such systems, in addition to the blister-monitoring sensors, the head or harvester can also include at least one temperature measuring element, such as a thermistor, for measuring the temperature of the skin or evacuated chamber.

The harvester body is configured for placement on a target region of a patient's skin and further adapted to form a sealing engagement with a head and define the chamber for application of negative pressure. In one embodiment, the harvester body further includes at least one alignment plate having a plurality of holes through which skin blisters can be raised in the presence of negative pressure; and a cutting plate having at least one cutting surface for cleaving skin blisters after they are formed within the chamber.

In another preferred embodiment, the harvestor includes a top alignment plate and a bottom alignment plate and the cutting plate is disposed therebetween. The top and bottom alignment plates can be joined together by a plurality of vertical posts that pass through slots in the cutting plate to maintain the fixed position of the top and bottom plates relative to each other while permitting movement of cutting plate. The top plate, bottom plate and cutting plate can each have a plurality of holes that are adapted to be concentrically aligned to facilitate blister formation. In certain embodiments, the holes of the top plate are larger than the holes of the bottom plate.

The cutting plate can include a plurality of holes suitable for concentric alignment with holes in the alignment plate in a first position to facilitate blister formation and a plurality of cutting surfaces suitable for cleaving blisters in a second position. The harvester can further include an actuator for moving the cutting plate from the first position to the second position and the actuator can configured to also at least partially retract the cutting plate following blister cleavage.

The sensor systems of the present invention can be disposed in proximity to the cutter mechanism (e.g., adjacent to, or incorporated into, the top plate or bottom plate to monitor blister formation). Signals from the sensor element(s) can be transmitted to a controller, e.g., a microprocessor or programmed logic unit, which can be disposed in the head, the harvester or in a remote console. Alternatively, the sensor elements can include a transmitter that wirelessly transmits information regarding blister formation to a remote terminal or controller.

Various other sensor mechanisms for monitoring blister formations can be used in lieu of an optical emitter-detector system. For example, distance sensing can be employed using laser, sonar or ultrasound techniques. In such embodiments, emitters and receivers can sit above the openings through which the blisters are pulled in the system. By recording the time it takes for the signal to return, the distance from the emitter and the top of the blister can be calculated. When this distance is reduced to be equal or less than a predetermined value, the skin is ready for harvesting. The controller can then shut off the blister forming elements of the harvester or alert the user that the blisters can be harvested.

In a further embodiment, ultrasound can also be used to produce a volume representation of the cavity in which the blisters are being pulled within the system. This can then be used to calculate the volume of the blisters by subtracting the measured volume from the start volume. Again, when a predetermined valve is reached, the device can alert the user that the skin is ready for harvesting or automatically shut off the blister forming elements of the harvester.

Alternatively, contact-based systems and methods can also be used in the invention. For example, load sensors can be placed above each harvest orifice (or at predetermined sites to reduce cost). When the blister contacts the load sensor the device can shut off or alert the user that the skin is ready for harvesting. In another embodiment, the system can periodically lower and retract the load sensors (so that the load sensor does not inhibit the blister from rising further or otherwise interfere with the application of negative pressure to the orifices).

In yet another embodiment. conductive systems and methods can be employed. For example, since skin is conductive, a touch panel can be placed within the harvester (or at predetermined positions). Once in contact with the skin in an acceptable number of locations or total area, the device can shut off or alert the user that the skin is ready for harvesting. As with the load sensor method, the capacitive sensor may need to be periodically lowered.

In yet another embodiment, changes in the volume of the chamber can be measured (e.g., by deadspace leak detection). For example, when a vacuum source is used to exert negative pressure on the internal chamber of the harvester, the chamber in which the blisters are being formed can be periodically vented. If the volume of the chamber is known, then the time it takes for the chamber pressure to reach a predetermined threshold (e.g., a specific negative pressure level) can be used to calculate the volume of the blisters that are protruding through the harvester and terminate the harvesting process or alert the user that the skin is ready for harvesting.

In yet another embodiment the sensor can be a colorimetric sensor capable of detecting changes in color, e.g., in a plate having the holes through which the blisters will be raised. When a sufficient portion of the sensor's field of view registers one or more colors associated with the skin or blister, a controller associated with the sensor can alert the user that the skin graft(s) are ready for harvesting—or automatically initiate steps to cut the blister(s).

The potential advantages of this invention in the context of suction blister devices can include (a) reducing the burden on the caregiver in terms of monitoring and constant visual checking, (b) providing more accurate determinations of when the blisters are in condition for harvesting, (c) reducing the time for harvesting since the system will alert the care giver as soon as the site is ready and/or (d) reducing discomfort for patient as system is currently monitored manually by removing the top of the device if the user cannot judge the state of blisters through the viewing window.

These and other aspects of the devices of the invention are described in the figures, description and claims that follow. While several improved design features have been individually described, such features are not mutually exclusive of each other. Any combination of design features disclosed herein can be used integrated into the devices of the invention. These design features and other aspects of the devices of the invention are described in the figures, description and claims that follow.

BRIEF DESCRIPTION OF THE DRAWINGS

FIG. 8 illustrates the load sensor prior to blister formation;

FIG. 9 is a schematic illustration of a load sensor detecting the formation of a blister;

FIG. 10 illustrates the distance sensor prior to blister formation;

FIG. 11 is a schematic illustration of a distance sensor detecting the presence of a blister;

DETAILED DESCRIPTION

The present invention generally relates to sensor systems for use in devices that can raise a blister (e.g., a suction blister) and cut the raised blister, i.e., a blister raising device integrated with a cutting member. Such devices are useful for harvesting skin grafts. In particular the devices and systems are adapted to infuse a fluid into skin at a donor site to enhance blister formation.

In certain embodiments, the devices according to the invention include a head portion that can be removably coupled to a harvester body that is positioned at the donor site of a subject's skin. The head portion and the body portion define a sealed chamber therebetween so that a fluid can be instilled and removed, and so that negative pressure can be applied to skin following fluid infusion. Although shown and described as part of the head portion, it should be clear that the coupler or conduit for fluid delivery and evacuation of the chamber can be part of either the head portion or the body portion and that the fluid and negative pressure can be applied separately via multiple couplings or via a single conduit as illustrated.

Figure 1A:
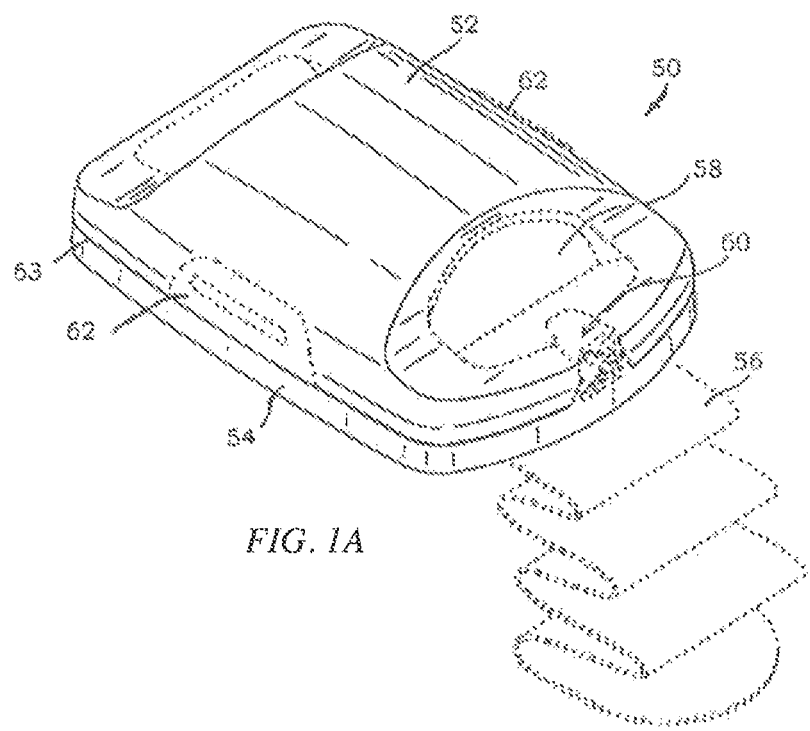
FIG. 1A is a schematic perspective view of a skin blister harvesting device according to the invention.

FIG. 1A is a schematic view of a skin graft harvester 50 for use in accordance with various aspects of the present teachings. In this illustrative embodiment, the harvest 50 includes a detachable head portion 52 and harvester body 54. The harvester body 54 is adapted for placement on a patient's skin at a donor site where skin grafts are to be obtained, e.g., on the inner thigh, and secured in place, for example, with strap 56 (shown in phantom). The head 52 can further include a heater (not shown) powered via a coupler 60 adapted to couple with a power source in a base unit (not shown). The head 52 further includes a seal 63 which permits a reduced pressure chamber to be formed when the head 52 and body 54 are joined together and the harvester 50 is coupled to a vacuum pump or other source of reduced pressure, e.g., via coupler 60 connecting the harvester 50 to its base unit. The head 52 can further include one or more windows 58 for observation of skin blisters being formed within the chamber by application of reduced pressure, heat or both. Once the blisters have been formed, the head 52 can be removed, e.g., by deactivating the source of reduced pressure and by actuation of release levers 62, which break the seal 63 and allow the head 52 to be lifted off the harvester body 54.

Additional details on harvesters useful in connection with the present invention can be found in U.S. patent application Ser. No. 13/839,518 filed Mar. 15, 2013; U.S. patent application Ser. No. 13/346,329 filed Jan. 9, 2012; U.S. patent application Ser. No. 13/436,318 also filed Jan. 9, 2012; U.S. patent application Ser. No. 13/014,737 filed Jan. 27, 2011; U.S. patent application Ser. No. 12/851,656 filed Aug. 6, 2010; U.S. patent application Ser. No. 12/851,621 filed Aug. 6, 2010; U.S. patent application Ser. No. 12/851,703 filed Aug. 6, 2010; and U.S. patent application Ser. No. 12/851,682 filed Aug. 6, 2010. The contents of each of the above-referenced related applications are herein incorporated by reference in their entireties.

Figure 1B:
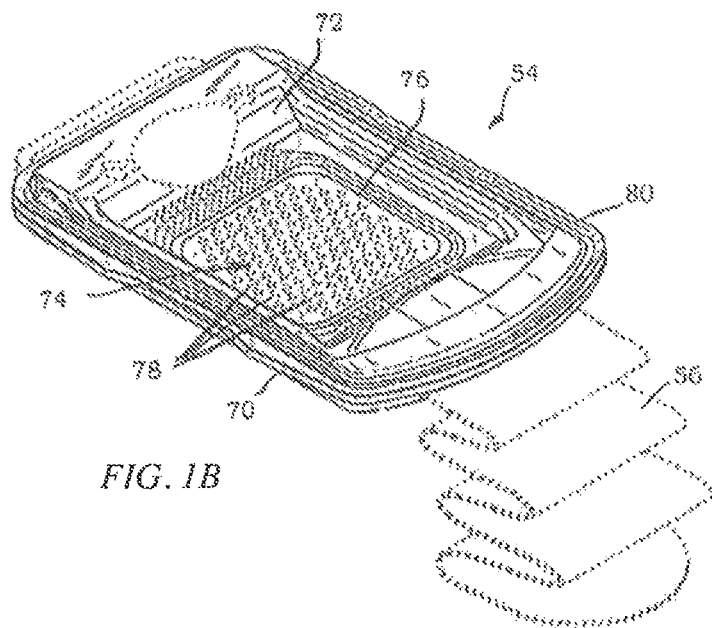
FIG. 1B is a schematic perspective view of a base portion of the skin blister harvesting device of FIG. 1A.
Figures 8, 9:
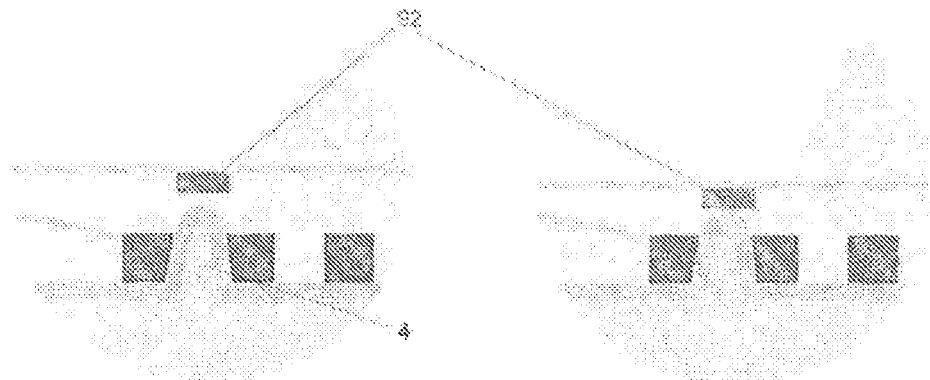
FIGS. 8 and 9 are schematic illustrations of an alternative sensor system based on load sensing.

FIG. 1B is a schematic view of the skin graft harvester 50 of FIG. 1A with the head 52 removed and the cutting mechanism 74 exposed. The harvester body 54 can include a base portion 70, a sled 72, and actuator handle 80. The cutting mechanism 74 can include a plurality of plates with initially aligned holes through which skin blisters are drawn by heat and/or application of suction when the head 52 is joined to the harvester body 54 and activated. Once the blisters are formed, they can be cleaved by the cutting mechanism 74. For example, below the top plate depicted in FIG. 8, one or more additional plates, e.g., a cutter plate and a bottom plate can be deployed with aligned holes. By actuation (e.g., pulling up) of handle 80, the sled 72 is caused to move horizontally such that one of the plates below the top plate, e.g., the "cutter plate" (not shown) also moves (because of its linkage to the sled 72), thereby occluding the alignment of holes 78 and cleaving the raised blisters from the donor's skin.

As explained in more detail below, the sensor systems of the present invention can be incorporated into either the harvester head 52 or harvester body 54—or both.

Figure 2A:
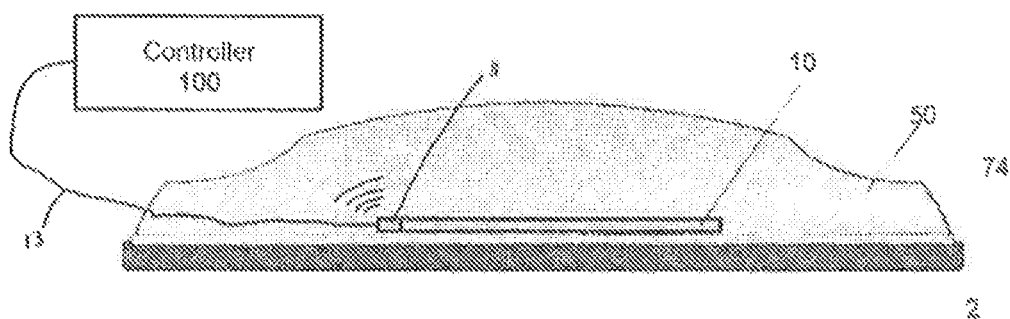
FIG. 2A is a schematic side view of a harvester device with a sensor system according to one embodiment of the invention.
Figure 2B:
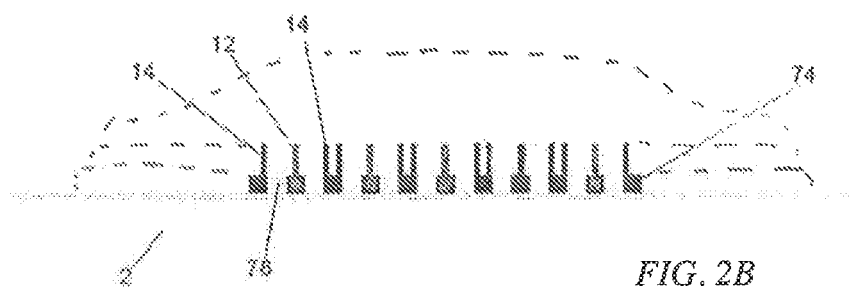
FIG. 2B is a schematic cross-sectional view of the harvester device of FIG. 2A.

FIGS. 2A and 2B are schematic illustrations of harvester device 50 having a cutter mechanism 74 in contact with a donor site of a patient's skin 2 and equipped with a non-contact blister sensor 10 to reduce burden and variability in deciding when a skin graft is ready to be harvested. The sensor is connected (e.g., by a wired connection 13 or wireless path via transceiver 11) to a controller 100 which can be part of the harvester or situated remotely (e.g., as part of the console that provides a source of negative pressure and/or current to heater elements (not shown) within the harvester. The controller 100 can be a dedicated device or a software application on general purpose computer, laptop, tablet or smart phone type device. The wireless connection can operate via a Bluetooth or other communication protocol.

As shown in the cross-sectional schematic view of FIG. 2B, The sensor 10 can be constructed of a matrix of non-contact proximity sensor elements (e.g., utilizing technology such as infrared or laser optics). The sensor elements can include emitters 12 and receivers 14. The sensor elements are disposed above or integrated into the cutting mechanism 74. When initially deployed the cutter mechanism has a plurality of align holes, through which skin blisters will be drawn by suction, heating or other manner.

Figure 3:
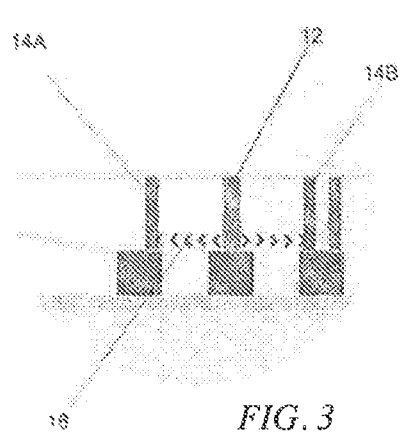
FIG. 3 is a schematic illustration of a sensor system employing a transmitter and receivers prior to blister formation.
Figure 4:
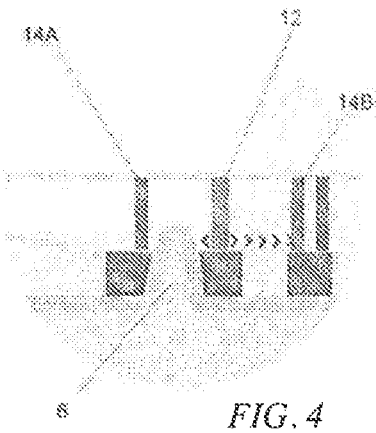
FIG. 4 is a schematic illustration of the sensor system of FIG. 3 detecting the formation of a blister.

As shown in FIGS. 3 and 4, each emitter 12 produces a signal 16 that can be received by a receiver 14. If emitter 12 emits multidirectional signal, it can be paired with multiple sensors, e.g., receivers 14A and 14B. (Possible emitter and receiver combinations arranged around holes 78 on the top plate 82 of a cutter mechanism can be seen in FIGS. 5-7 with the receivers omitted from FIGS. 6 & 7 for simplicity).

When receiver 14A does not receive an expected signal (FIG. 4) it can be assumed that the direct line of travel between the emitter 12 and receiver 14A has been broken and that therefore the blister 4 has achieved a sufficient height to be ready for harvesting.

Figure 5:
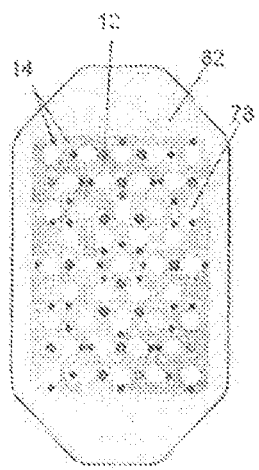
FIG. 5 is a schematic illustration of a pattern of transmitter and receiver elements that can reduce the number of transmitters.
Figure 6:
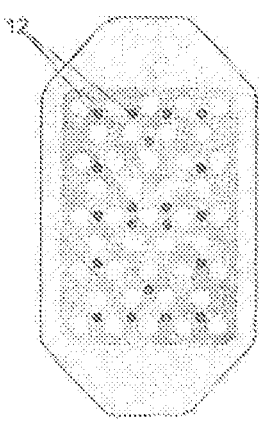
FIG. 6 is a schematic illustration of an alternative pattern of transmitters.
Figure 7:
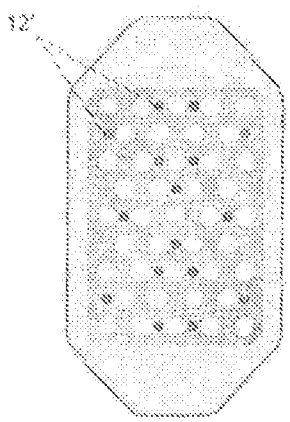
FIG. 7 is a schematic illustration of only the transmitter elements in the pattern of FIG. 5.

By using multidirectional or omnidirectional emitters paired with multiple sensors, as shown in FIG. 5-7, the complexity and cost is lessened by reducing the number of components in the system. The signal can be a continuous beam or a series of timed pulses to reduce power consumption (and also limit irradiation of skin as well as the graft to be harvested).

Due to the dynamic nature of some intended donor sites, it may be necessary to take repeated readings for each emitter and receiver arrangement before an alert is given that the site is ready for harvesting. In certain embodiments, the system can be configured to ensure that a pre-assigned number of paired sensor arrangements (emitter and receiver) are in a 'ready' state before giving an alert to the user that the site is ready for harvesting.

When the conditions have been met and the system is sure that the skin is ready for harvesting, the device can instruct the user of this status. Depending on the complexity of the device, the system may even indicate the next steps in the process.

In an alternative embodiment, the sensors can be contact sensors. For example, load sensors can be placed above each harvest orifice (FIG. 8); or at predetermined sites to minimize cost. When the blister contacts the load sensor 92 the device can alert the user that the skin is ready for harvesting. The system may need to periodically raise and lower the load sensors (FIG. 9) to avoid interference with blister formation during the application of negative pressure within the chamber. Moreover, conductivity sensors can be used in lieu of (or in conjunction with) load sensors. As skin is conductive, the sensor can be a conduction touch panel that can be placed within the harvester (or at predetermined positions). Once in contact with the skin in an acceptable number of locations or total area, the device can alert the user that the skin is ready for harvesting. As with the load sensor method, the capacitive sensor may need to be periodically raised and lowered.

Figures 10, 11:
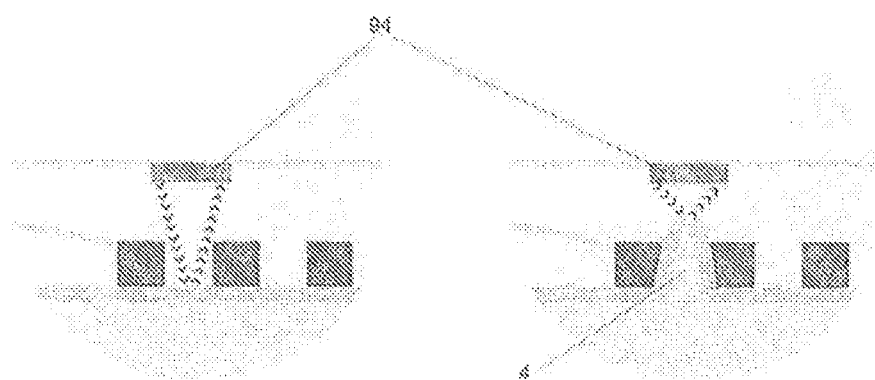
FIGS. 10 and 11 are schematic illustrations of an alternative sensor system based on distance sensing.

In another alternative embodiment, the sensors can be distance sensing sensors. Utilizing laser, sonar or ultrasound techniques, a sensor (e.g., an emitter and receiver pair) can sit above the openings through which the blisters are pulled in the system. By recording the time it takes for the signal to return to the distance sensor 94 (FIG. 10), the distance from the emitter and the top of the blister 4 can be calculated. When this hits a predetermined time, the skin is ready for harvesting (FIG. 11). In some embodiments, a single emitter and multiple receivers can be employed. Alternatively, multiple emitters and a single receiver can be used. The signals from the receiver(s) can be multiplexed or averaged to determine when a sufficient number of holes have been filled with blisters ready for harvesting.

In yet another embodiment, the sensor can employ "volume sensing" techniques. For example, ultrasound can be used to produce a volume representation of the cavity in which the blisters are being pulled within the system. This can then be used to calculate the volume of the blisters by subtracting the measured volume from the start volume. When the ultrasound signal reaches a predetermined threshold the device can alert the user that the skin is ready for harvesting. Alternatively, changes in the volume of the chamber can be determined by deadspace leak detection. By utilizing the vacuum source, the cavity in which the blisters are being formed can periodically be vented. If the leak within the cavity is known, then utilizing the time it takes for the cavity pressure to hit a predetermined threshold the system can calculate the volume of the blisters that are protruding through the harvester and alert the user the skin is ready for harvesting.

Figure 12:
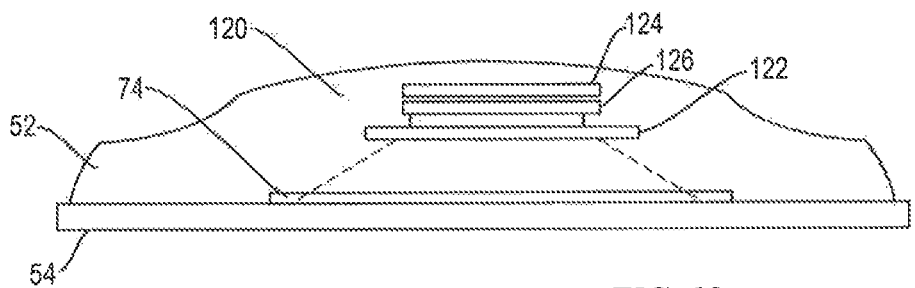
FIG. 12 is a schematic illustration of a color sensor detecting the presence of a blister.

In yet another embodiment, as shown in FIG. 12 the sensor can be a colorimetric sensor 120 capable of detecting changes in color, e.g., in a plate having the holes through which the blisters will be raised. The sensor can include a color photo detector 122 (or an array of such detectors) and an optional lens 124 (for widening the view of view). When a sufficient portion of the sensors field of view registers one or more colors associated with the skin or blister, a controller associate with the sensor can alert the user that the skin graft(s) are ready for harvesting—or automatically initiate steps to cut the blister(s). The colorimeter can further include filters 126 to preferentially pass colors associated with skin tones (or skin components such as melanin). The detector can be deployed within the device's chamber. Alternatively, light from the chamber can be collected via a waveguide or optical fiber (or fiber bundle) and transmitted to a detector outside of the device.

Figure 13A:
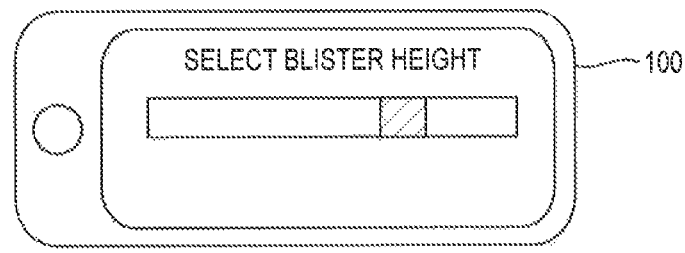
FIG. 13A is a schematic illustration of a controller display showing a user interface for selecting a desired blister height.

The device/sensor can be configured to allow the user to define the blister height before initiating graft formation. This can be done mechanically by adjusting the space between the sensor and the forming hole, or electronically by adjusting the calibration of the sensor for proximity, pressure, reflection, time to receive a sound wave, etc. For example, as shown in FIG. 13A, the controller 100, e.g., a smartphone app, can communicate with the sensor to select a desired height.

Figure 13B:
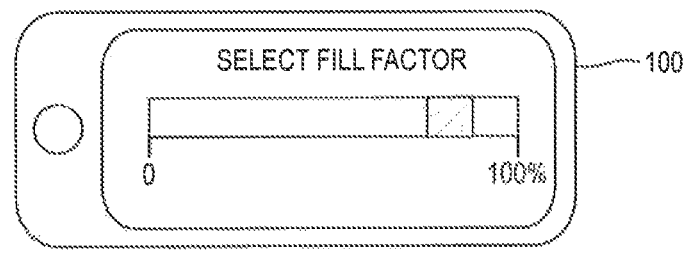
FIG. 13B is a schematic illustration of a controller display showing a user interface for selecting a desired blister fill factor.
Figure 13C:
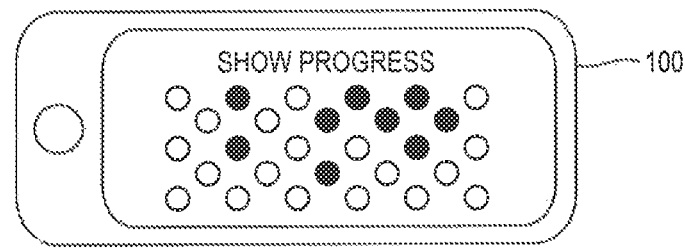
FIG. 13C is a schematic illustration of a controller display showing a user interface for showing progress in successful blister formation.

The device/sensor can also be configured to allow the user to define the minimal number of successfully formed grafts that need to be formed before alerting the clinician that the grafts are ready (50%, 70%, 100%). In addition, the device can count the number of grafts formed and either display as a total, a percentage of the total, or in a light grid pattern (one light for each graft, changing from red to green when formed). This allows the user to decide if they have enough grafts and in the pattern/orientation suitable for them. For example, as shown in FIG. 13B, the controller 100, e.g., a smartphone app, can communicate with the sensor to select a desired fill factor to be obtained or, as shown in FIG. 13C, the controller 100 can monitor and display the progress of blister formation so that the user can determine when to initiate graft formation.

The term "load sensor," as used herein, is intended to encompass pressure transducers, touch sensors, piezometers and other piezoelectric devices, force sensors, force sensing variable resistors and/or capacitors and like devices which can determine pressure or contact based on changes in force or electrical or magnetic behavior.

The term "conductivity sensor," as used herein, is intended to encompass devices that can measure or determine changes in light, electrical resistance, capacitance and/or impedance, associated with the presence of skin within or near a target site.

The term "in proximity" encompasses situations wherein objects are close to each other as well situations where objects are in contact with each other. Closeness is not absolute quantity but rather denotes a distance wherein an object, e.g., a sensor, can perform its intended function.

References and citations to other documents, such as patents, patent applications, patent publications, journals, books, papers, web contents, have been made throughout this disclosure. All such documents are hereby incorporated herein by reference in their entirety for all purposes.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The invention claimed is:

1. A method for preparing a skin graft, the method comprising:
   applying a blister cutting device to a donor site on a subject's skin;
   applying a negative pressure within the device to thereby raise at least one blister at the donor site;
   monitoring formation of the at least one blister with a sensor, and
   transmitting information from the sensor to a controller configured to reduce or terminate the negative pressure.

2. The method of claim 1, further comprising transmitting information from the sensor to alert a user when the at least one blister has reached a state suitable for harvesting.

3. The method of claim 1, further comprising transmitting information from the sensor to a controller.

4. The method of claim 1, further comprising transmitting information from the sensor to a controller configured to activate a cutter device that cleaves the at least one blister.

5. The method of claim 1, wherein the sensor comprises at least one emitter-receiver pair within the blister cutting device, and further comprising emitting a signal from the emitter and receiving the signal with the receiver.

6. The method of claim 5, further comprising emitting at least one of an electromagnetic radiation or acoustic waves, detecting at least one of a returned electromagnetic radiation or a returned acoustic wave, determining presence of a skin blister based on analyzing the returned electromagnetic radiation or the returned acoustic wave.

7. The method of claim 1, further comprising disposing the sensor in a close proximity of a growing blister and monitoring the formation of the growing blister by detecting changes in electrical, magnetic or optical behavior of a sensor element.

8. The method of claim 1, wherein the sensor is a load sensor, and further comprising disposing the sensor in close proximity of a growing blister and monitoring the formation of the growing blister by assessing pressure asserted by the growing blister on the load sensor.

9. The method of claim 1, wherein the sensor is a conductivity sensor, and further comprising disposing the sensor in close proximity of a growing blister to monitor the formation of the growing blister.

10. The method of claim 1, wherein the sensor is a color sensor, and further comprising monitoring formation of the at least one blister by detecting changes in color within the device using the color sensor.

11. The method of claim 1, wherein the sensor is a colorimetric sensor, and further comprising using the sensor to detect changes in color in a plate having the holes through which the at least one blister is raised.

12. The method of claim 1, wherein the sensor is an acoustic sensor, and further comprising monitoring formation of the at least one blister by detecting changes in acoustics within the device using the acoustic sensor.

13. The method of claim 1, wherein the sensor is an ultrasound sensor, and further comprising monitoring formation of the at least one blister by detecting changes in an acoustic signature or image within the device using the ultrasound sensor.

14. The method of claim 1, wherein the sensor is a vacuum sensor, and further comprising monitoring formation of the at least one blister by detecting changes in the negative pressure within the device using the vacuum sensor.

15. The method of claim 1, wherein the sensor is an vacuum sensor and further comprising monitoring formation of the at least one blister by using the vacuum sensor to deduce volume changes within the device by measuring time required to reach a negative pressure level within the device.

16. The method of claim 1, further comprising applying an adhesive substrate to the at least one blister, cleaving the at least one blister, and removing the substrate from the cutting device to harvest the skin graft.

17. The method of claim 1, wherein the blister cutting device comprises at least one fixed plate and at least one movable cutter plate, each plate having a plurality of holes through which the at least one blister is raised when the plurality of holes of the at least one fixed and at least one movable cutter plates are aligned, and further moving the at least one movable cutter plate to disrupt alignment of the plurality holes and from the subject's skin at the donor site.

18. The method of claim 1, wherein the blister cutting device further comprises a plate with holes through which the at least one blister is raised, and further comprising delivering a warm hypotonic fluid to a chamber within the device to cause a portion of the subject's skin exposed to the chamber via the plate holes to assimilate the fluid and be pulled into the chamber through the holes to raise the at least one blister.

19. A method for preparing a skin graft with a device comprising a device body, a sealing head member, at least one fixed plate and at least one movable cutter plate, each plate comprising a plurality of holes, wherein as assembled the holes in the plates are aligned within the body, the method comprising:
   connecting the device to a donor site on a subject's skin;
   joining the sealing head member and the device body together to define a sealed chamber;
   applying negative pressure to the sealed chamber to pull a portion of the subject's skin at the donor site into the sealed chamber through the plurality of holes and raise a plurality of blisters;
   monitoring formation of at least one blister with a sensor to detect when the blisters are in a condition suitable for harvesting;
   unsealing the chamber to expose the at least one blister;
   applying an adhesive substrate to the at least one blister exposed within the chamber;
   actuating the at least one movable cutter plate to disrupt alignment of the plurality of holes and cut the at least one blister; and
   removing the substrate together with the at least one blister.

20. A method for preparing a skin graft, the method comprising:

applying a blister cutting device to a donor site on a subject's skin;

applying a negative pressure within the device to thereby raise at least one blister at the donor site;

monitoring formation of the at least one blister with a sensor, and transmitting information from the sensor to a controller configured to activate a cutter device that cleaves the at least one blister.

21. The method of claim 20, further comprising disposing the sensor in a close proximity of a growing blister and monitoring the formation of the growing blister by detecting changes in electrical, magnetic or optical behavior of a sensor element.

22. The method of claim 20, wherein the sensor is a load sensor, and further comprising disposing the sensor in close proximity of a growing blister and monitoring the formation of the growing blister by assessing pressure asserted by the growing blister on the load sensor.

23. A method for preparing a skin graft, the method comprising:

applying a blister cutting device to a donor site on a subject's skin, the blister cutting device further comprising a plate with holes through which at least one blister is raised;

delivering a warm hypotonic fluid to a chamber within the device to cause a portion of the subject's skin exposed to the chamber via the plate holes to assimilate the fluid and be pulled into the chamber through the holes to raise the at least one blister;

monitoring formation of the at least one blister with a sensor.

* * * * *